United States Patent [19]
Norton

[11] Patent Number: 5,430,787
[45] Date of Patent: Jul. 4, 1995

[54] COMPTON SCATTERING TOMOGRAPHY

[75] Inventor: Stephen J. Norton, Gaithersburg, Md.

[73] Assignee: The United States of America as represented by the Secretary of Commerce, Washington, D.C.

[21] Appl. No.: 985,115

[22] Filed: Dec. 3, 1992

[51] Int. Cl.⁶ .......................................... G01N 23/203
[52] U.S. Cl. ......................................... 378/87; 378/6; 378/901
[58] Field of Search ...................... 378/6, 86, 87, 901

[56] References Cited

U.S. PATENT DOCUMENTS

| | | | |
|---|---|---|---|
| 3,243,589 | 3/1966 | Sinclair | 378/86 |
| 3,927,318 | 12/1975 | Macovski | 378/6 |
| 3,936,638 | 2/1976 | Gibbons | 378/5 |
| 4,229,651 | 10/1980 | Danos | 378/87 |
| 4,839,808 | 6/1989 | Koval et al. | 364/413.24 |
| 4,850,002 | 7/1989 | Harding et al. | 378/87 |
| 5,125,017 | 6/1992 | Lempriere | 378/86 |
| 5,155,365 | 10/1992 | Cann et al. | 250/363.02 |

OTHER PUBLICATIONS

"Three-Dimensional Density Field Determination by External Stationary Detectors and Gamma Sources Using Selective Scattering", N. Kondic et al, Proc. 2nd Int. Topl. Mtg. Nuclear Reactor Thermal-Hydraulics, vol. II, pp. 1443-1455 (1983).

"On the Solution of the Inverse Problem of Radiation Scattering Imaging" Hussein et al, Nuclear Science and Engineering, 92, pp. 341-349, 1986.

"Compton Scatter Imaging of Transverse Sections: Corrections for Multiple" Battista et al, Phys. Med. Biol., 1977, vol. 22, No. 2, pp. 229-244.

"Dual-energy Compton Scatter Tomography" Harding et al, Phys. Med. Biol., 1986, vol. 31, No. 5, pp. 477-489.

"An Electronic Imaging Technique for One-Sided X-Ray Inspection" Berger et al, 1989 ASME Pressure Vessel and Piping Conf., Jul. 23-27.

Primary Examiner—Paul M. Dzierzynski
Assistant Examiner—David Vernon Bruce
Attorney, Agent, or Firm—Michael de Angeli

[57] ABSTRACT

Apparatus and methods for Compton scattering tomography employ a source of monoenergetic gamma rays and a detector capable of detecting the energy of scattered photons and determining the detector location both disposed on one side of an object to be imaged. Based on analysis of the measurement of the energy of the detected photons and the detector locations, a circle of possible scattering locations is determined as to each scattering event. By performance of a number of experiments as a function of detector location and energy, the density of the object can be reconstructed by filtering and back-projecting the data to yield an image responsive to variation in the density of the material of the object to be imaged.

10 Claims, 3 Drawing Sheets

COMPTON SCATTERING TOMOGRAPHY

BACKGROUND OF THE INVENTION

1. Field of the Invention

This invention relates to tomographic imaging of solid objects and the like by Compton scattering. More particularly, the invention relates to methods and apparatus for providing images indicative of variations in density of the interior of solid objects and the like, wherein the examination process may be carried out entirely from one side of the object.

2. Description of the Prior Art

In recent years, much attention has been paid to the problem of imaging the interior of solid bodies. Most commonly, x-rays, that is, high energy photons or gamma rays, are used in a transmission mode. In the pioneer work of Röntgen, and as still practiced today, x-rays are passed through an object to be imaged, such as a patient's limb, and imaged on a photographic plate disposed opposite the source. Variations in the density in the x-rays collected by the plate correspond to variation in the attenuation of the x-rays by the structures of the limb. Thus, for example, bone shows up more darkly on a x-ray plate than do skin and fleshy tissue, because the x-rays pass through the flesh without substantial attenuation, but are more effectively absorbed by bone. More particularly, the absorption of the x-rays is effectively a function of the density of the materials through which the beam passes.

More recently, in order to obtain a more detailed picture of the interior of structures, so-called computer assisted tomography ("CAT") or computed tomography ("CT") scanning processes have been developed. In these processes, x-rays are again employed to irradiate a subject to be imaged, and are collected on a sensor (typically a solid-state sensor) on the opposite side of the object. A large number of images are taken with respect to a large number of source locations and detector locations. These images are combined and "back-projected" using well-known computerized "tomographic" imaging techniques to provide images amounting to two-dimensional maps of variation in the density of three-dimensional objects, such as the interior of a patient's skull. Again, as different types of tissues and structures within the body exhibit variation in their x-ray absorption, these images can be used to effectively image the various structures.

As noted, both conventional x-ray imaging techniques and CAT or CT scanning are normally performed in a transmissive mode, that is, the source is on one side of the object and the solid-state detector or photographic plate on the other. Transmissive-mode imaging has certain significant limitations; in particular, access is required to both sides of the object to be imaged. Similarly, both x-ray "still" imaging and CT or CAT scanning techniques are absorptive, that is, variations in x-ray absorptivity of the various materials appear as variations in the gray-scale density of the image.

A further method of imaging known to the prior art involves "Compton scattering". Compton scattering occurs when an x-ray or other high energy photon or gamma ray from a source is scattered by an electron, either free or bound to an atom. A distinct angle $\alpha$ is formed between the incident and scattered x-ray. This angle $\alpha$ is known to be characteristic of the difference in energy of the incident and scattered rays. Stated differently, the art recognizes that the difference in energy of the incident and scattered rays is directly related to the included angle $\alpha$ formed between their respective ray paths.

The rate at which the x-rays are scattered from a particular region is indicative of its density; since Compton-scattering of x-rays takes place from electrons of individual atoms, more scattering takes place when the material is more dense. This fact is known to the prior art to be useful in generating images of body structures and the like using Compton scattering. See Battista et al, "Compton Scatter Imaging of Transverse Sections: Corrections for Multiple Scatter and Attenuations", *Phys. Med. Biol.*, Vol. 22, No. 2, 229–244 (1977); Harding et al, "Dual-energy Compton Scatter Tomography", *Phys. Med. Biol.*, Vol. 31, No. 5, 477–489 (1986); and U.S. Pat. No. 3,927,318 to Macovski.

Compton scattering may also be employed under experimental conditions such that relatively acute angles $\alpha$ are formed between the incident and scattered rays, such that the source and detector can be placed on the same side of a relatively massive object. In this way, the requirement of access to both sides of the object, as is necessary in transmissive-mode x-radiography or CAT-scanning, can be avoided. Imaging systems of this type have been disclosed. See, for example, Berger et al, "An Electronic Imaging Technique for One-Sided X-Ray Inspection", 1989 *ASME Pressure Vessel and Piping Conf.*, (1989); U.S. Pat. No. 3,243,589 to Sinclair; and U.S. Pat. No. 5,125,017 to Lempriere.

The characteristic angle a between the incident and scattered x-rays in Compton scattering has also been used in transmissive systems for determining the density of various objects. See U.S. Pat. No. 3,936,638 to Gibbons.

U.S. Pat. No. 4,229,651 to Danos shows a imaging system employing Compton scattering of photons at between about 60° and about 120° from the angle of incidence.

As indicated above, in Compton scattering an x-ray (or gamma ray) is scattered by an electron and the scattered ray suffers some energy loss. A characteristic included angle $\alpha$ is formed between the paths of the incident and scattered gamma rays. The angle $\alpha$ is a function of the difference between the energies of the incident and scattered gamma rays. The art is aware that the detection of a scattered gamma ray of a particular energy at a particular detector location responsive to an incident gamma ray of known energy allows the determination that the scattering location is on an "isogonic" line, that is, a line forming a circular path defined as the locus of all points connected to the source and detector location by ray paths making the included constant scattering angle $\alpha$. (See FIG. 2, discussed below.) See Kondic et al, "Three-Dimensional Density Field Determination by External Stationary Detectors and Gamma Sources Using Selective Scattering" Proc. 2nd *Int. Topl. Mtg. Nuclear Reactor Thermal-Hydraulics*, Vol. II, p. 1443 (1983). Kondic teaches at page 1446 that "meshes" of isogonic lines, that is, lines corresponding to various possible scattering locations within a volume, can be used for example to locate the interfaces between liquid and gas. However, Kondic et al do not teach an efficient method of imaging the interior of a solid body responsive to Compton scattering.

In "On the Solution of the Inverse Problem of Radiation Scattering Imaging", Hussein et al, *Nuclear Science and Engineering*, vol. 92, 341–349 (1986), there is disclosed a method for imaging the density distribution of two-phase flow. The basic technique disclosed includes detection of Compton scattered gamma rays, and determination of possible scattering locations responsive to determination of the scattering angle by measuring the energy of the scattered ray. However, the imaging method disclosed involves the simultaneous solution of a large set of simultaneous equations. This process is undesirably complex.

OBJECTS AND SUMMARY OF THE INVENTION

It is therefore an object of the invention to provide a method and apparatus for imaging the interior of a solid body using Compton scattering techniques, wherein both a source of irradiating gamma rays and a detector of scattered gamma rays may be disposed on the same side of an object to be imaged.

It is a further object of the invention to provide a method and apparatus for performing a filtered back-projection reconstruction of an image of an interior of an object, where a source of gamma rays is used to irradiate the object and a detector of gamma rays is used to detect Compton-scattered gamma rays, and where the source and detector are disposed on the same side of the object.

These and other objects of the invention appearing in the discussion below are satisfied according to the present invention, whereby a beam of monoenergetic gamma rays is employed to irradiate an object to be inspected. A detector capable of detecting individual scattered gamma rays and measuring their individual energies is employed to detect gamma rays having been Compton-scattered. The energies of the detected gamma rays are recorded, together with the respective detector locations. A number of similar experiments are performed, each involving the steps of irradiating the object from one or more source locations and detecting the scattered gamma rays at a plurality of detector locations. The energies of each of the scattered gamma rays are determined and used to identify possible scattering locations lying on circular paths within the object. The possible scattering locations corresponding to each of the source and detector locations and the differing energies of the scattered gamma rays are employed for reconstructing an image by a filtered back-projection algorithm. The areas of maximum probability of possible scattering correspond to regions of high density of materials within the object, while areas of less probable scattering locations correspond to areas of lower density within the object.

BRIEF DESCRIPTION OF THE DRAWINGS

The invention will be better understood if reference is made to the accompanying drawings, in which.

DESCRIPTION OF THE PREFERRED EMBODIMENTS

Figure 1:
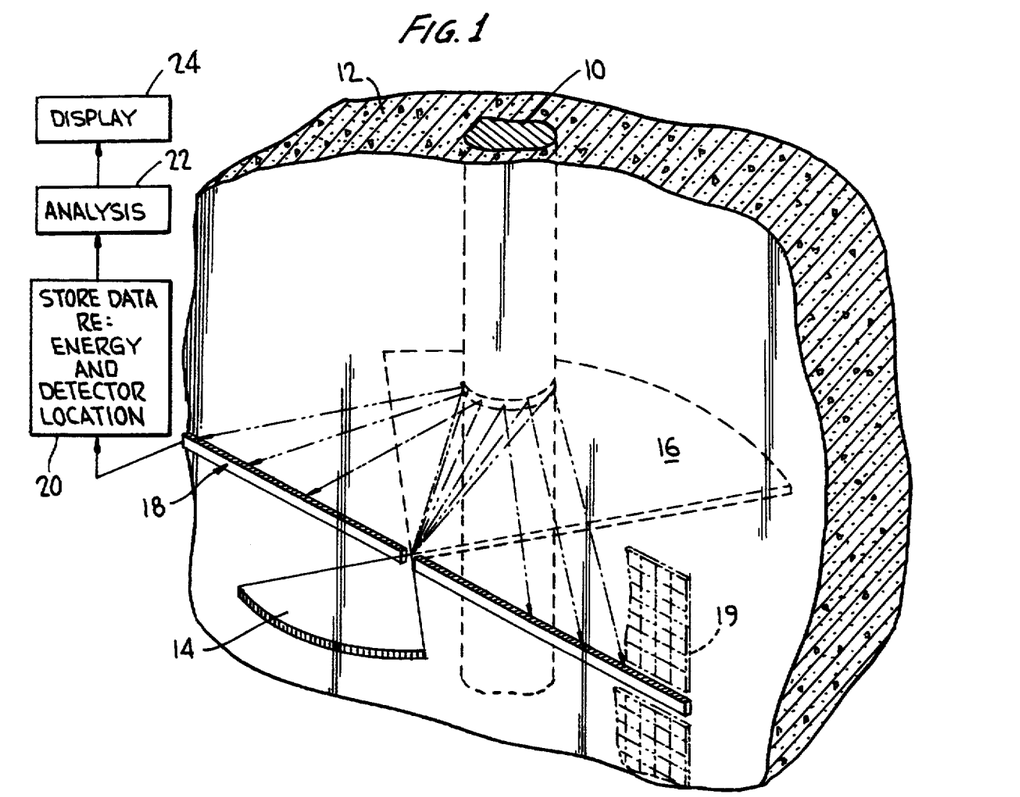
FIG. 1 is a three-dimensional partially cut-away schematic view of the apparatus used according to the invention in examination of, for example, a large composite structure.

As indicated, it is an object of the invention to provide an image responsive to variation in the density of a solid object using one or more gamma ray sources and energy- and position-sensitive detectors disposed on one side thereof. FIG. 1 shows schematically a perspective view of a suitable source and detector arrangement. In this example, suppose it is desired to monitor the integrity of steel bars 10 reinforcing a concrete wall indicated generally at 12. According to the invention, a source 14 emitting a fan-shaped beam 16 of monoenergetic gamma rays typically in the range of several hundred keV is juxtaposed to the wall 12. In this energy regime Compton scattering is the dominant scattering mechanism. Thus, the source 14 emits a large quantity of vertically-collimated gamma rays all of essentially identical energy, such that the beam has a relatively well defined two-dimensional shape as indicated at 16. However, it should be noted that while a fan-shaped beam is shown, the invention also can readily be practiced using a "pencil" or directional beam swept over some volume of the object to be imaged. Alternatively, the invention may be practiced with a source which irradiates a solid volume of the object. The requirement that the source 14 be monoenergetic will normally be most readily satisfied by using a radioactive source emitting gamma rays of characteristic energy.

The gamma rays from source 14 pass into the object as at 16 and are Compton-scattered from electrons of atoms of the materials therein. Where the material of the object being imaged is more dense, a relatively larger proportion of the gamma rays are scattered toward the surface where they may be detected by a detector 18. Detector 18 is capable of measuring the energies of each detected gamma ray, and of noting the specific location at which each gamma ray is detected. Where the source 14 is juxtaposed to a steel reinforcement bar 10, a relatively substantial fraction of the incident gamma rays can be expected to be Compton scattered and detected by detector 18. A somewhat lesser fraction of the incident gamma rays will be scattered from the less dense concrete 12 and will also be detected by the detector 18. More specifically, the relative proportion of gamma rays re-radiated from the steel reinforcement 10 and the concrete 12 is a function of the respective densities of these materials, since Compton scattering is a probabilistic effect varying with the density of electrons in the material.

The detected gamma rays are processed to yield data indicative of the probability of their having been scattered from any particular point within the structure. Typically, all the data are acquired simultaneously, i.e., data are gathered with respect to scattered gamma rays of all energies and detected at all positions along detector 18. A number of similar experiments may be carried out with sources and detectors at a number of locations. The position- and energy-dependent data are processed using a filtered back-projection algorithm to yield an image of the interior of the object, that is, a tomographic image, wherein the probability of scattering is proportional to the density of the material at that point.

The detector 18 may comprise a number of discrete sensors multiplexed to a computer or the like for simultaneous measurement of the energy of a detected gamma ray and recording of the position at which it was detected. Alternatively, detector 18 could be a so-called gamma ray semiconductor drift detector, as used in high energy physics and in gamma ray astronomy. Such a detector consists of a continuous strip of semiconductor material such as germanium operating on the charge transport principle. An incident photon creates a pulse of charge that drifts along the length of the strip under the influence of an applied electric field. The size of the pulse is proportional to the photon energy and the arrival time determines its relative position. Such detectors, together with suitable signal processing and data recording elements indicated schematically at 20 and 22, are thus capable of simultaneously measuring the energy of the photon and detecting its position. The image is provided on a display 24. A two-dimensional detector array (as indicated at 19) can be provided if it is desired to form a three-dimensional image in a single experiment.

Figure 2:
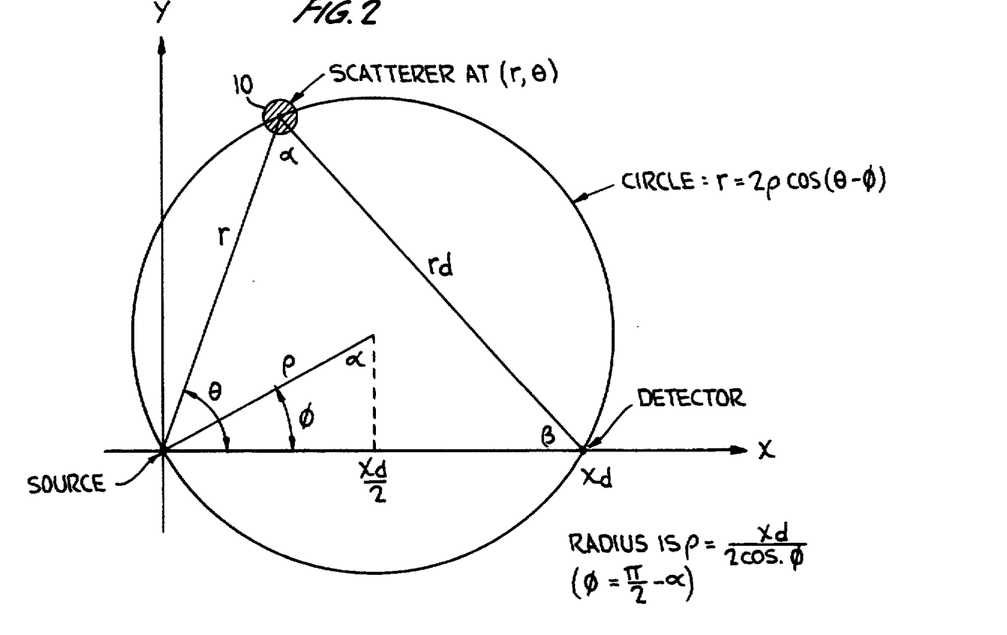
FIG. 2 illustrates terminology used in mathematical explanation of the invention.

FIG. 2 shows the geometry of a single source and detector combination. A source at the origin emits gamma rays over a wide solid angle. A photon of initial energy $E_\alpha^{(0)}$ is scattered by an electron at $(r,\theta)$ and is detected with energy $E_\alpha$ by a detector at $x_d$. The scattering angle $\alpha$ is related to the energy $E_\alpha$ of the detected photon by the Compton scattering formula:

$$E_\alpha = \frac{E_\alpha^{(0)}}{1 + k(1 + \cos\alpha)} \quad (1)$$

where $k=E_\alpha^{(0)}/mc^2$ and m is the electron mass. Thus each detected photon is characterized by the two variables $x_d$ and $E_\alpha$, or equivalently from Eq. (1), by $x_d$ and $\alpha$, since the detected energy $E_\alpha$ is a function of the scattering angle $\alpha$. Thus, from Eq. (1) it is apparent that a photon detected at $x_d$ with energy $E_\alpha$ could have been scattered at any point connectable to the source and detector location $x_d$ by lines forming the included angle $\alpha$.

Geometric considerations indicate that scatterers which could satisfy these conditions can be located anywhere along a "circle of constant energy" expressed by the equation $r=2\rho \cos(\theta-\phi)$, where, as indicated by FIG. 2, $\phi=\pi/2-\alpha$, and the radius of the circle is $\rho=x_d/2 \cos\phi$. That is, the circle of constant energy is defined by the locus of all possible scattering locations of a particular gamma ray, that is, the locus of all points connectable by straight lines to the origin and $x_d$ and forming the included angle $\alpha$.

Thus, any gamma ray arriving at a particular detector location $x_d$ with a certain energy $E_\alpha$ is known to have been scattered from a point around the unique circle defined by that energy and detector location (FIG. 2). When multiple gamma rays are emitted from the source, the measurement of the detected gamma ray intensity (or gamma ray count) can be expressed as a weighted path integral of the Compton scattering cross-section (i.e., a weighted average of the cross-section) around this circle. The Compton scattering cross-section is in turn proportional to the material's electron density; thus, the reconstructed image may be regarded as a quantitative map of electron density. According to the invention, measurements of scattered gamma rays are recorded at multiple detector locations and with respect to a range of energies. Path-integrals of electron density over many overlapping circles are then measured. According to a further aspect of the invention, an efficient tomographic algorithm for reconstructing the electron density from these circular path-integral measurements is provided.

According to the invention, a large number of measurements are made with the source at the origin and a detector at, e.g., $x_d$. If there is a notable density variation within an essentially two-dimensional plane irradiated by gamma rays from the source, there will be a like variation in the proportion of possible scattering locations on circles of constant energy where that plane intersects region(s) of relative density variation. Stated differently, if the plane irradiated by the gamma rays includes an object of higher density, such as a steel bar 10, comparatively more gamma rays will be re-radiated with energies $E_\alpha$ corresponding to reflection at possible scattering locations in the plane along a circular line running through the high density material, than from locations on paths extending through only less dense surrounding material.

Gamma rays of differing energy and recorded at different detector locations correspond to scattering circles of different radii passing through the source and detector. Accordingly, in response to a set of measurements of scattered gamma ray energy and detector location, a set of overlapping circles may be plotted, each intersecting different regions of the object. Stated differently, the back-scattered intensity with respect to a particular detector located at $x_d$ and to gamma rays of energy $E_\alpha$ corresponds to radiation scattered from somewhere around the unique scattering circle defined by the variables ($x_d$, $E_\alpha$). As noted, this measurement can be expressed in the form of a (weighted) integration, or path integral, of the object's electron density around this unique circle. Therefore, according to the invention, the scattering data are recorded as a function of detector position and energy, and are then combined using a filtered back-projection technique to yield an image indicative of variations in the density of the object.

Figure 3:
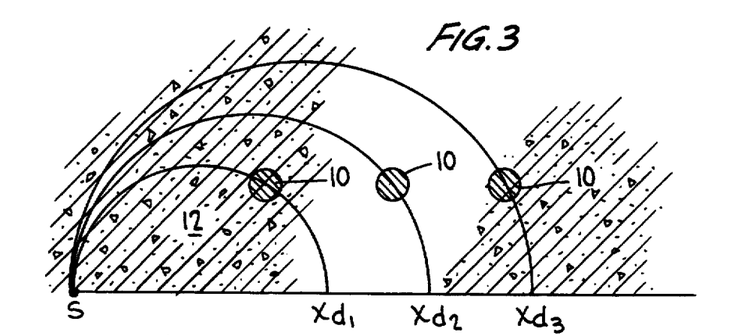
FIGS. 3, 4 and 5 represent successive stages in forming an image of variation in density of materials within a structure according to the method of the invention.
Figures 4, 5, 6:
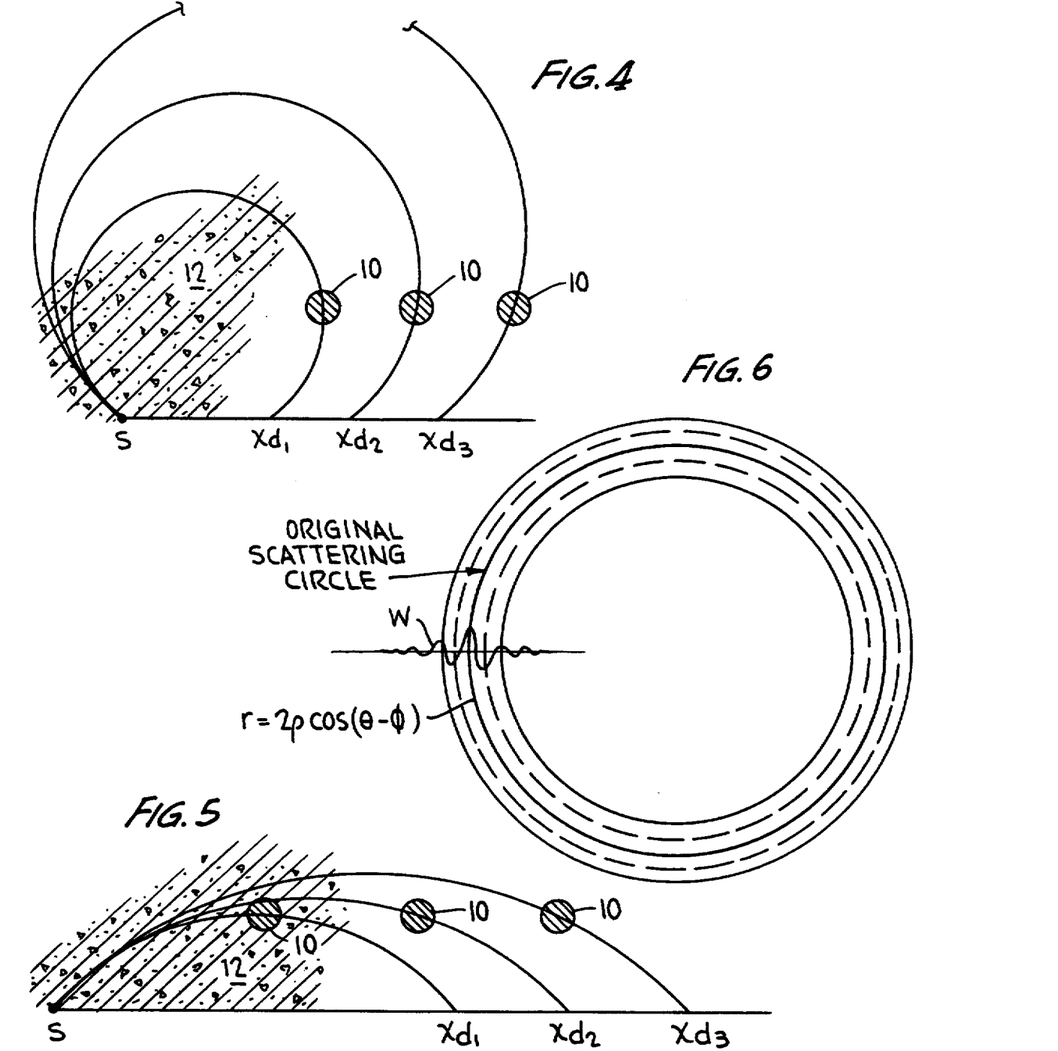
FIG. 6 is a diagram illustrating filtering employed in practice of the method of the inventions.

The results of a succession of scattering measurements at different energies and detector locations are shown diagrammatically in FIGS. 3, 4 and 5. In these figures, three sets of distinct circles of different radii (corresponding to different energies and detector locations) intersect the same three regions of high density, e.g., metal bars reinforcing a concrete structure. It is this overlapping of the circular paths that allows a mathematical "sorting out" of the data to distinguish the higher density of the metal bars from the lower density of the embedding material. To obtain an accurate and quantitative image of electron density, many overlapping circular paths are required, as discussed below.

FIG. 3 shows a number of circular paths corresponding to possible scattering locations extending between the source location S and three detector locations $x_{d1}$, $x_{d2}$ . . . $x_{dn}$. The circles shown are "circles of constant energy" corresponding to detection of gamma rays of differing characteristic energy. That is, each circle shown in FIG. 3 corresponds to a number of possible scattering locations for gamma rays of particular energy. If the density of the object is inhomogeneous, for example, if the object includes a steel bar 10 in a matrix of concrete 12, a proportionately larger number of gamma rays will be scattered from the material of higher density. Thus, a detector at $x_d$ will detect more gamma rays having been scattered from possible scattering locations on circular paths intersecting the location of the steel bar 10. However, the steel bar may lie anywhere on the "circles of constant energy" of possible scattering locations. That is, measurements taken with respect to a single source and detector location are insufficient to locate the steel bar.

Turning now to FIG. 4, suppose that a second set of measurements are taken corresponding to different energies and different detector locations. Again, more scattered gamma rays will be detected associated with circles of constant energy passing through the reinforcing bars 10, compared to circles passing through the less-dense concrete matrix 12. The intersection of the second set of circles of constant energy through the reinforcing bar in FIG. 4 again produces more intense scattering and provides some indication of the location of the dense object. However, these two sets of measurements alone would not be sufficient to generate a satisfactory image responsive to the variation in density of the object.

FIG. 5 shows a third set of circles of constant energy representing measurements of scattered gamma rays at a third set of energies and detected at a third set of detector locations. When these are plotted together with the circles of FIGS. 3 and 4, the locations of the reinforcing bars are reasonably well defined. That is, at this stage the locations of the bars 10 are fairly well established at the intersection of the densest group of circles of constant energy. The region of their intersection represents the region including the maximum probability of scattering, that is, the maximum material density. If additional similar measurements are made, and their corresponding scattering circles are superimposed, each weighted in proportion to the number of photons scattered from that circle, a crude picture of the object's variation in density will result. However, by optimally processing the data, in a manner to be described, before superimposing the circles ("back-projecting along the circles"), a correct, quantitative image of the object's density is obtained.

Stated more generally, according to the invention, measurements are made at many energies and detector locations (and optionally at plural source locations), corresponding to measurements of the integrated scattering cross-section (or electron density) around many overlapping circles. The data are then used according to the invention to recover a quantitative image of electron density. As shown below, the process of the invention effectively filters the data and then back-projects the filtered data around the circles of constant energy reconstructing the electron density.

The following provides a mathematically more rigorous disclosure of the invention.

As above, we assume an energy and position sensitive detector lying along the x-axis (FIG. 2). Gamma rays are emitted from a fan-beam source at x=0 into the upper x-y plane (we assume collimation within this plane). Let $I(x_d, E_\alpha)$ denote the number of photons of energy $E_\alpha$ recorded at the detector position $x_d$. The scattering angle $\alpha$ of the photon is then inferred from the energy $E_\alpha$ by means of the Compton scattering formula:

$$E_\alpha = \frac{E_\alpha^{(0)}}{1 + k(1 + \cos\alpha)} \quad (1)$$

where $E_\alpha^{(0)}$ is the energy of the emitted photon, $k = E_\alpha^{(0)}/mc^2$ and m is the electron mass. Thus each detected photon is characterized by the two variables $x_d$ and $E_\alpha$, or equivalently from Eq. (1), by $x_d$ and $\alpha$, since the detected energy $E_\alpha$ determines the scattering angle $\alpha$. The equations simplify if we change variables from $x_d$ and $\alpha$ to $\rho$ and $\phi$, where $x_d = 2\rho\cos\phi$, and $\phi = \pi/2 - \alpha$. Thus, we may express the data as a function of $\rho$ and $\phi$ instead of $x_d$ and $E_\alpha$: $I(x_d, E_\alpha) = I(\rho,\phi)$.

We denote the electron density in the x-y plane (in polar coordinates) by the function $f(r,\theta)$. Then the measurement $I(\rho,\phi)$ can be shown to be related to the electron density by the following path integral:

$$I(\rho,\phi) = \int_{c(\rho,\phi)} f(r,\theta)w(r,\theta;\rho,\phi)dl \quad (2)$$

where:

$C(\rho,\phi)$ signifies the circle of "constant energy" expressed by the equation $r = 2\rho\cos(\theta-\phi)$;

dl is an element of path length around circle $C(\rho, \phi)$; and $w(r,\theta;x_d,E_\phi)$ is a weighting function that takes into account a number of effects, including (1) the 1/r spreading of the photons from the source, (2) any inhomogeneity in the irradiating gamma ray beam, (3) the dependence of the differential cross-section on the scattering angle $\alpha$ subtended by source and detector and (4) the solid angle subtended by the finite-sized detector from the scattering point.

We also note that w can be used to take into account attenuation of the photons from the source to the scatterer and back to the detector. In this case, w will itself depend implicitly on the electron density $f(r,\theta)$. Correction of the image responsive to attenuation is discussed below.

In an idealized case, in which perfect spatial and energy resolution of the detector are assumed, the circle of constant energy $C(\rho,\phi)$ has infinitesimal thickness. In reality, the detector has finite spatial and energy resolution, and the circle will broaden into a circular band of small but finite thickness. In this case, Eq. (2) will become an integration over this circular band. By comparison, the prior art as exemplified by the Macovski patent treated the data collection processes as equivalent to calculation of line integrals along straight lines.

Equation (2) can be solved using Fourier techniques to yield an explicit expression for the image $f(r,\theta)$ in terms of the measurements $I(\rho,\phi)$. Although this formula was derived assuming an idealized detector, its use with data recorded by realistic detectors having finite energy and spatial resolution merely produces images of finite resolution.

Processing of data according to the invention to yield an image is comparable to convolution back-projection algorithms used in transmission computed tomography, except that according to the invention back-projection takes place around the circular paths $C(\rho,\phi)$, instead of along straight lines, as in transmission tomography.

More specifically, the imaging formula of the invention can be expressed as an integral transform of the following form:

$$\rho(r,\theta) = w_1(r,\theta) \int d\rho \int d\phi I(\rho,\phi) h(r,\theta;\rho,\phi) \quad (3)$$

where:

$$h(r,\theta;\rho,\phi) = w_2(\rho,\phi) \int d\zeta |\zeta| A(\zeta) \exp[i\zeta(r - 2\rho\cos(\theta-\phi))]. \quad (4)$$

Here $w_1(r, \theta)$ and $w_2(\rho,\phi)$ are known weighting functions. In Eq. (4) $A(\zeta)$ plays the role of a spatial-frequency filter function, such that $|\zeta|A(\zeta) \to 0$ as $|\zeta| \to \infty$. The simplest case is a rectangular filter given by $A(\zeta)=1$ for $|\zeta|<\zeta_{cutoff}$ and $A(\zeta)=0$ for $|\zeta|>\zeta_{cutoff}$, where $\zeta_{cutoff}$ is a spatial-frequency bandlimit. The effect of filtering using the function $A(\zeta)$ is to sharpen the image at the expense of signal-to-noise ratio. A similar type of filtering is frequently employed in conventional (transmission) x-ray computed tomography. Allowing the cutoff $\zeta_{cutoff}$ to increase improves image resolution at the expense of the signal-to-noise ratio, and vise versa. This basic trade-off is also encountered in more conventional forms of tomography.

The filtering expressed by equation (4) can be physically interpreted as illustrated in FIG. 6. FIG. 6 is obtained by plotting equation (4) as a function of r and $\theta$ for fixed $\rho$ and $\phi$; the latter variables specify the scattering circle. An original scattering circle $r=2\rho\cos(\theta-\phi)$ is broadened into a set of closely spaced concentric circles having positive and negative weights. Thus, moving transversely (radially) to the original circular path at any position therearound, one would encounter negative sidelobes on either side of the central peak corresponding to the original circular path, as illustrated by the wavelet W in FIG. 6. When the circles of constant energy corresponding to the data, after being thus modified or "filtered", are finally superimposed or "back-projected", the negative sidelobes cancel unwanted contributions from other overlapping circles, yielding the correct image.

The process of filtering the circles of constant energy and back-projecting the filtered circles to image density variations in an object is mathematically expressed by equations (3)–(5). A generally corresponding process of filtering and back-projection also forms the basis of the well-known "filtered back-projection" algorithm employed in conventional x-ray tomography, but there the back-projection is performed over straight lines rather than over circular paths, as in the practice of the present invention.

Equations (3) and (4) provide the basis of an exceptionally efficient image reconstruction algorithm. Implementation of these equations to yield an image is within the skill of the art. In effect, Eq. (2) represents an integration of the density of the material along a filtered circle of constant energy denoted by $C(\rho,\phi)$. Eqs. (3) and (4) represent a filtered back-projection algorithm which reconstructs the density. The nature of the back-projection operation can be more clearly seen by substituting Eq. (4) into (3) and by defining $f'=f/w_1$ and $I'=Iw_2$. This gives:

$$f'(r,\theta)=\int d\rho \int I'(\rho,\phi) h'[r-2\rho\cos(\theta-\phi)] \quad (5)$$

where $h'(.)$ is the integral on the left side of Eq. (4). Eq. (5) represents an effective back-projection operation on $I'(\rho,\phi)$ around the circle defined by $r-2\rho\cos(\theta-\phi)=0$. Eqs. (3) and (4) or, equivalently, Eq. (5) can also be evaluated in the Fourier domain.

As noted, the effect of filtering pursuant to Equations (3)–(5) is to sharpen the image density variations by processing the data so that the scattering circles have a "wavelet-like" radial variation, with a central "peak" at the original radius surrounded by "valleys".

Figure 7:
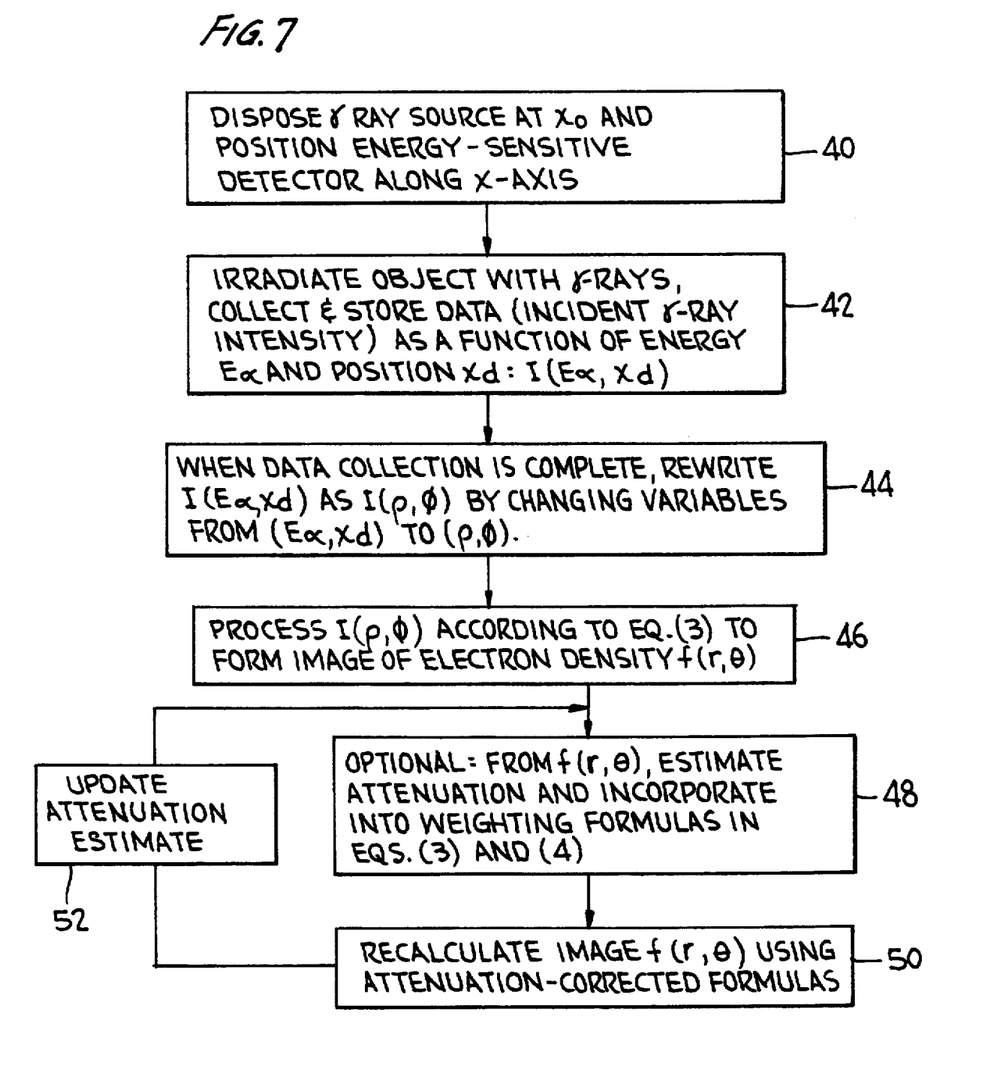
FIG. 7 is a flowchart showing the steps in one method of practice of the invention.

FIG. 7 is a flow chart of typical steps in the imaging process according to the invention. In this exemplary flow chart, the process begins at step 40, when the gamma ray source is disposed at a initial location $x_0$ with an array of energy-sensitive detectors disposed along the x-axis (see FIG. 2). Alternatively, as indicated, a single semiconductor drift detector with position and energy sensitivity can be disposed along the x-axis. The variable $x_d$ is used to identify the position of an incident photon along the detector. In step 42, the object is irradiated with gamma rays, while the number (or intensity) of Compton-scattered gamma rays are recorded by the detector and stored as data points. The energy, $E_\alpha$, and the position, $x_d$, of detection of each recorded gamma ray is stored. That is, the recorded intensity, $I(E_\alpha, x_d)$, is stored as a function of energy $E_\alpha$ and detector location $x_d$. As noted, the variables $E_\alpha$ and $x_d$ determine a unique circle of constant energy, and $I(E_\alpha, x_d)$ is given by a (weighted) line-integral of the electron density around this circle [see Eq. (2)].

In step 44, a change of variables from $(E_\alpha, x_d)$ to $(\rho,\phi)$ is performed, where $x_d=2\rho\cos\phi$ and $\phi=\pi/2-\alpha$; here $\rho$ is the scattering circle radius and $\phi$ is the angular position of its center [see FIG. 2]. With this change in variables, the recorded data $I(E_\alpha,x_d)$ is equivalently written $I(\rho,\phi)$. In step 46, the image reconstruction is carried out by substituting $I(\rho,\phi)$ into Eq. (3) and performing the indicated integration.

In effect, the data stored with respect to the detected gamma rays is used in step 44 to determine the scattering angle $\alpha$ for each detected gamma ray. The scattering angle $\alpha$ for each ray is used to determine the locations of possible scatterers along a circle of constant energy, i.e., the locus of points from which each individual gamma ray might have been scattered. Conveniently, a datum or "count" is recorded corresponding to each detected gamma ray at locations in a two-dimensional array, wherein the elements of the array correspond to possible scattering locations within the object, so that the values in each element of the array correspond to the total number of scattering events possible with respect to the corresponding volume in the object. At the conclusion of step 44 the magnitude of each sum in the array will represent the total probability of possible scattering events within the corresponding volume of the object being inspected. These sums thus correspond to the density of the object at the corresponding location.

At step 46, when data collection is complete, an image is generated, following the rule of filtering and back-projecting (superimposing) the data $I'(\rho,\phi)$ according to equation (5). The image will illustrate a "slice" through the object, in which the darker pixels will correspond to denser portions of the object imaged.

To appreciate a further aspect of the invention, it is important to realize that equations (3) and (4) were derived under the assumption that attenuation along the incident and reradiated gamma ray paths, from the source to the scatterer and back to the detector, can be neglected as a first approximation, or considered a constant value independent of electron density. However, equations (3) and (4) can also be employed in an iterative fashion to take into account an electron-density dependent attenuation, in the following manner. First, an image of $f(r,\theta)$ is formed under the assumption of no electron-density dependent attenuation, as in step 46. Next, from this image, the attenuation is estimated as a function of total path length, and incorporated into the weighting functions $w_1(r,\theta)$ and $w_2(\rho,\phi)$ in Eqs. (3) and (4), at step 48. Finally, a new image is formed at step 50 in the manner just described, using the "attenuation corrected" formulas. This process can be iterated several times, as indicated at 52. The result is a self-consistent image of electron density, $f(r,\theta)$, that accounts for both scattering and attenuation in the measurements. Whether such an attenuation correction is needed will depend on the type of object or material under inspection as well as other factors, such as the gamma ray source energy. In some cases, iteration may be unnecessary for acceptable images.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method for imaging the density of material in the interior of an object to be inspected, comprising the steps of:

(a) providing a monoenergetic source of gamma rays;
   (b) providing a position- and energy-sensitive detector;
   (c) disposing said source at a first source location exterior to one side of said object, and employing said source to irradiate said object with gamma rays;
   (d) employing said detector to detect gamma rays having been Compton scattered at one or more detector location(s) disposed exterior to said one side of said object;
   (e) measuring the energy of the detected gamma rays, and recording the locations at which the gamma rays were detected;
   (f) determining a locus of possible scattering locations of the detected rays responsive to the measured energy of the detected rays and the locations at which the rays were detected;
   (g) determining variation in the density of material in the object responsive to summation of the loci of scattering locations determined in said step (f) by filtered back-projection of the data recorded in step (c) as a function of energy and location of detection of the detected gamma rays; and
   (h) imaging the variation in density thus determined.

2. The method of claim 1, comprising the further steps of moving said source to plural source locations and reperforming said steps (c)–(g) with respect to said plural source locations.

3. The method of claim 1, wherein in each performance of said step (f) said loci of possible scattering locations are determined to lie on a circle having a radius $\rho$ determined responsive to the measured energy of the detected gamma rays.

4. The method of claim 3, wherein said radius $\rho$ is determined according to the following:

$$\rho = \frac{x_d}{2} \cos\phi$$

wherein:

$x_d$ = spacing of the source from the detector, and
$\phi = \pi/2 - \alpha$, where
$\alpha$ is derived by solution of $$E_\alpha = \frac{E_\alpha^{(0)}}{1 + k(1 + \cos\alpha)}$$

wherein:

$E_\alpha$ = energy of detected gamma ray;
$E_\alpha^{(0)}$ = energy of irradiating gamma ray; and $k = E_\alpha^{(0)}/mc^2$.

5. The method of claim 1, wherein the filtered back-projection step with respect to the loci of possible scattering locations is performed with respect to each detector location by evaluation of line integrals with respect to detected gamma rays having particular energy, such that the integration effectively sums the possible gamma ray scattering locations along a circular path of radius $\rho$, and the result of each integration is indicative of the total electron density in said object along the corresponding path.

6. The method of claim 5, wherein said line integrals are evaluated responsive to the following relationship between the data recorded in step (e), $I(\rho,\phi)$, and the unknown electron density, $f(r,\theta)$:

$$I(\rho,\phi) = \int_{c(\rho,\phi)} f(r,\theta) W(r,\theta;\rho,\phi) dl$$

wherein:

$C(\rho, \phi)$ refers to a circle of possible scattering locations defined by $r = 2\rho \cos(\theta\phi)$;
dl is an element of path length around circle $C(\rho, \phi)$; and
$W(r, \theta; \rho, \phi)$ is a weighting function.

7. The method of claim 6, wherein the density of the object is imaged by display of the reconstructed function $f(r,\theta)$ obtained by processing the data $I(\rho,\phi)$, whereby the data is filtered and then back-projected around circular paths of constant energy.

8. The method of claim 1, comprising the further step of estimating the attenuation of gamma rays in passage between said source, said scattering locations and detector locations, and employing the estimated attenuation in said imaging step.

9. An apparatus for imaging the density of material in the interior of an object to be inspected, comprising:

a monoenergetic source of gamma rays disposed at a first source location exterior to one side of said object, to irradiate said object with gamma rays;
   detector means for detecting gamma rays having been Compton scattered at known detector locations disposed exterior to one side of said object,
   means for measuring the energy of the detected gamma rays;
   means for determining a locus of possible scattering locations of each detected ray responsive to its measured energy;
   means for determining variation in the density of the material of the object responsive to effective summation of the loci of possible scattering locations, wherein said loci of possible scattering locations lie along circular paths of constant energy; and
   means for imaging the variation in density thus determined, comprising means for filtering and back-projecting the loci of possible scattering locations at image locations corresponding to the circular paths, thus providing visible indication of variation in the density of material in the object.

10. The apparatus of claim 9, wherein said means for filtering and back-projection comprise means for evaluating the following relationship between data $I(\rho,\phi)$, responsive to the energy of the detected gamma rays and the locations at which the gamma rays are detected, and the unknown electron density, $f(r,\theta)$:

$$I(\rho,\phi) = \int_{c(\rho,\phi)} f(r,\theta) W(r,\theta;\rho,\phi) dl$$

wherein:

$C(\rho, \phi)$ refers to a circle of possible scattering locations defined by $r = 2\rho \cos(\theta - \phi)$;

$dl$ is an element of path length around circle $C(\rho,\phi)$; and $W(r, \theta; \rho, \phi)$ is a weighting function; and wherein:

$$\rho = \frac{x_d}{2} \cos\phi$$

wherein:

$x_d$ = spacing of the source from the detector, and
$\phi = \pi/2 - \alpha$, where
$\alpha$ is derived by solution of $$E_\alpha = \frac{E_\alpha^{(0)}}{1 + k(1 + \cos\alpha)}$$

wherein:
$E_\alpha$ = energy of detected gamma ray;
$E_\alpha^{(0)}$ = energy of irradiating gamma ray; and
$k = E_\alpha^{(0)}/mc^2$.

* * * * *